United States Patent [19]

Allen et al.

[11] Patent Number: 4,920,016

[45] Date of Patent: Apr. 24, 1990

[54] LIPOSOMES WITH ENHANCED CIRCULATION TIME

[75] Inventors: Theresa M. Allen, Edmonton, Canada; Alberto Gabizon, San Francisco, Calif.

[73] Assignee: Linear Technology, Inc., Menlo Park, Calif.

[21] Appl. No.: 132,136

[22] Filed: Dec. 18, 1987

Related U.S. Application Data

[63] Continuation-in-part of Ser. No. 946,415, Dec. 24, 1986, abandoned.

[51] Int. Cl.[5] .................... A61K 37/22; A61K 9/66; B01J 13/02

[52] U.S. Cl. .................... 424/450; 264/4.3; 264/4.6; 424/1.1; 424/94.3; 428/402.2; 436/829; 514/885

[58] Field of Search .............. 428/402.2; 424/450; 436/829; 514/885

[56] References Cited

U.S. PATENT DOCUMENTS

| | | | |
|---|---|---|---|
| 2,870,179 | 1/1959 | Jacini | 260/403 |
| 4,416,872 | 11/1983 | Alying et al. | 514/8 |
| 4,460,577 | 7/1984 | Moro et al. | 424/79 X |
| 4,515,736 | 5/1985 | Deamer | 424/1.1 X |
| 4,565,696 | 1/1986 | Heath et al. | 424/450 |
| 4,598,051 | 7/1986 | Papahadjopoulos et al. | 436/829 X |
| 4,684,625 | 8/1987 | Eppstein et al. | 424/450 X |

FOREIGN PATENT DOCUMENTS 0146710 9/1982 Japan ..................... 514/78

*Primary Examiner*—Richard D. Lovering
*Attorney, Agent, or Firm*—Peter J. Dehlinger

[57] ABSTRACT

A composition of liposomes which contain an entrapped pharmaceutical agent and are characterized by (a) liposome sizes predominantly between about 0.07 and 0.5 microns; (b) at least about 50 mole percent of a membrane-rigidifying lipid, such as sphingomyelin or neutral phospholipids with predominantly saturated acyl chains; and (c) between about 5–20 mole percent of a glycolipid selected from the group consisting of ganglioside $GM_1$, saturated phosphatidylinositol, and monogalactosyl stearate. The liposomes show high blood/RES tissue distribution ratios, and are effective for drug administration to tumors via intravenous drug delivery.

11 Claims, 2 Drawing Sheets

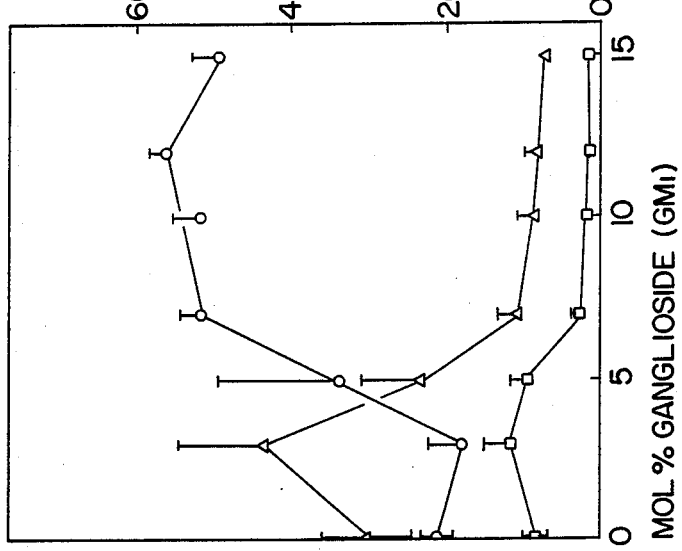
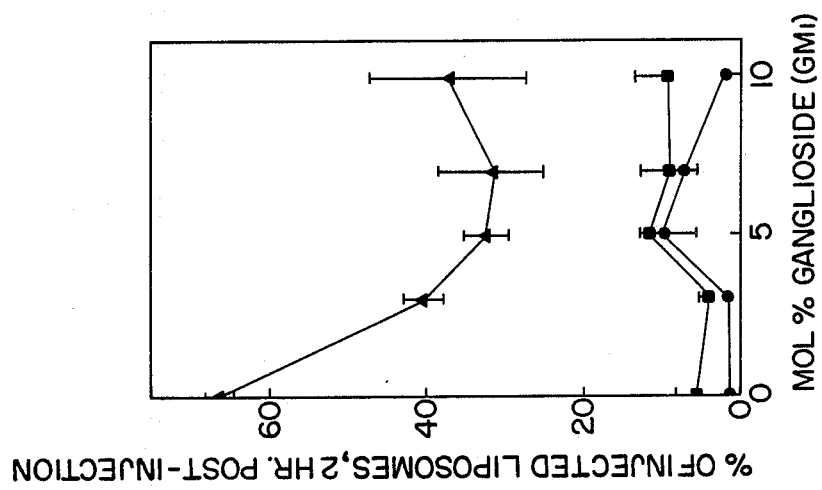
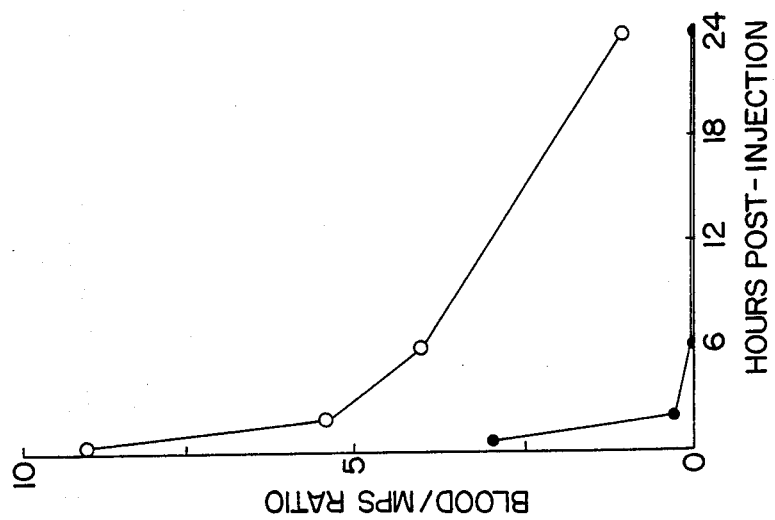
FIG. 2B
FIG. 2A
FIG. 1

LIPOSOMES WITH ENHANCED CIRCULATION TIME

This application is a continuation-in-part of co-pending U.S. patent application for "Liposomes with Enhanced Circulation Time", Ser. No. 946,415, filed 12/24/86, now abandoned.

FIELD OF THE INVENTION

The present invention relates to liposome therapeutic compositions, and particularly to liposomal formulations which have enhanced circulation time in the bloodstream, when administered intravenously.

References

1. Allen, T. M. (1981) Biochem. Biophys. Acta 640, 385397.
2. Allen, T. M., and Everest, J. (1983) J. Pharmacol. Exp. Therap. 226, 539–544.
3. Altura, B. M. (1980) Adv. Microcirc. 9, 252–294.
4. Alving, C. R. (1984) Biochem. Soc. Trans. 12, 342344.
5. Ashwell, G., and Morell, A. G. (1974) Adv. Enzymology 41, 99–128.
6. Czop, J. K. (1978) Proc. Natl. Acad. Sci. U.S.A. 75: 3831.
7. Durocher, J. P., et al (1975) Blood 45: 11.
8. Ellens, H., et al. (1981) Biochim. Biophys. Acta 674, 10–18.
9. Gregoriadis, G., and Ryman, B. E. (1972) Eur. J. Biochem. 24, 485–491.
10. Gregoriadis, G., and Neerunjun, D. (1974) Eur. J. Biochem. 47, 179–185.
11. Gregoriadis, G., and Senior, J. (1980) FEBS Lett. 119, 43–46.
12. Greenberg, J. P., et al (1979) Blood 53: 916.
13. Hakomori, S. (1981) Ann. Rev. Biochem. 50, 733–764.
14. Hwang, K. J., et al (1980) Proc. Natl. Acad. Sci. U.S.A. 77: 4030.
15. Jonah, M. M., et al. (1975) Biochem. Biophys. Acta 401, 336–348.
16. Juliano, R. L., and Stamp, D. (1975) Biochem. Biophys. Res. Commun. 63, 651–658.
17. Karlsson, K. A. (1982) In: Biological Membranes, vol. 4, D. Chapman (ed.) Academic Press, N.Y., pp. 1–74.
18. Kimelberg, H. K., et al. (1976) Cancer Res. 36, 2949–2957.
19. Lee, K. C., et al, J. Immunology 125: 86 (1980).
20. Lopez-Berestein, G., et al. (1984) Cancer Res. 44, 375–378.
21. Okada, N. (1982) Nature 299: 261.
22. Poznansky, M. J., and Juliano, R. L. (1984) Pharmacol. Rev. 36, 277–336.
23. Richardson, V. J., et al. (1979) Br. J. Cancer 40, 3543.
23. Saba, T. M. (1970) Arch. Intern. Med. 126, 1031–1052.
25. Schaver, R. (1982) Adv. Carbohydrate Chem. Biochem. 40: 131.
26. Scherphof, T., et al. (1978) Biochim. Biophys. Acta 542, 296–307.
27. Senior, J., and Gregoriadis, G. (1982) FEBS Lett. 145, 109–114.
28. Senior, J., et al. (1985) Biochim. Biophys. Acta 839, 1–8.
29. Szoka, F., Jr., et al (1978) Proc. Natl. Acad. Sci. U.S.A. 75: 4194.
30. Szoka, F., Jr., et al (1980) Ann. Rev. Biophys. Bioeng. 9: 467.
31. Woodruff, J. J., et al (1969) J. Exp. Med. 129: 551.

BACKGROUND OF THE INVENTION

Liposome delivery systems have been proposed for a variety of drugs. For use in drug delivery via the bloodstream, liposomes have the potential of providing a controlled "depot" release of a liposome-entrapped drug over an extended time period, and of reducing toxic side effects of the drug, by limiting the concentration of free drug in the bloodstream. Liposome/drug compositions can also increase the convenience of therapy by allowing higher drug dosage and less frequent drug administration. Liposome drug delivery systems are reviewed generally in Poznansky et al.

One limitation of intravenous liposome drug delivery which has been recognized for many years is the rapid uptake of blood-circulating liposomes by the mononuclear phagocytic system (MPS), also referred to as the reticuloendothelial system (RES). This system, which consists of the circulating macrophages and the fixed macrophages of the liver (Kupffer cells), spleen, lungs, and bone marrow, removes foreign particulate matter, including liposomes, from blood circulation with a half life on the order of minutes (Saba). Liposomes, one of the most extensively investigated particulate drug carriers, are removed from circulation primarily by Kupffer cells of the liver and to a lesser extent by other macrophage populations.

A variety of studies on factors which effect liposome uptake by the RES have been reported. Early experiments, using heterogeneous preparations of multiamellar liposomes (MLV) containing phosphatidylcholine (PC) and cholesterol (CH) as their principal lipid constituents, demonstrated that these liposomes are rapidly removed from circulation by uptake into liver and spleen in a biphasic process with an initial rapid uptake followed by a slow phase of uptake (Gregoriadis, 1974; Jonah; Gregoriadis, 1972; Juliano). Half-time for removal of MLV from circulation was on the order of 5–15 min. following intraveneous (IV) injection. Negatively charged liposomes are removed more rapidly from circulation than neutral or positively charged liposomes. Small unilamellar liposomes (SUV) are cleared with half-lives approximately three-to four-fold slower than MLV (Juliano; Allen, 1983). Uptake of liposomes by liver and spleen occurs at similar rates in several species, including mouse, rat, monkey, and human (Gregoriadis, 1974; Jonah; Kimelberg, 1976; Juliano; Richardson; Lopez-Berestein).

Liposomes which are capable of evading the RES would have two important benefits. One is the increased liposome circulation time in the blood, which would both increase the pharmacokinetic benefits of slow drug release in the bloodstream, and also provide greater opportunity for tissue targeting where the liver, spleen, and lungs are not involved. The second benefit is decreased liposome loading of the RES. In addition to the role of the RES in removing foreign particles, the RES is involved in several other functions, including host defense against pathogenic microorganisms, parasites, and tumor cells, host responses to endotoxins and hemorragic shock, drug response, and responses to circulating immune complexes (Saba, Altura). It is important, therefore, in liposome administration via the bloodstream, to avoid compromising the RES seriously, by massive short-term or accumulated liposome uptake.

One approach which has been proposed is to increase liposome circulation time by increasing liposome stability in serum. This approach is based on studies by one of the inventors and others which have shown that factors which decrease leakage of liposome contents in plasma also decrease the rate of uptake of liposomes by the RES (Allen, 1983; Gregoriadis, 1980; Allen, 1981; Senior, 1982). The most important factor contributing to this effect appears to be bilayer rigidity, which renders the liposomes more resistant to the destabilizing effects of serum components, in particular high density lipoproteins (Allen, 1981; Scherphof). Thus, inclusion of cholesterol in the liposomal bilayer can reduce the rate of uptake by the RES (Gregoriadis, 1980; Hwang; Patel, 1983; Senior, 1985), and solid liposomes such as those composed of distearoylphosphatidylcholine (DSPC) or containing large amounts of sphingomyelin (SM) show decreased rate and extent of uptake into liver (Allen, 1983; Ellens; Senior, 1982; Hwang).

However, this approach appears to have a limited potential for increasing liposome circulation times in the bloodstream. Studies carried out in support of the present invention, and reported below, indicated that 0.1–0.2 micron liposomes containing optimal membrane-rigidifying liposome formulation are predominantly localized in the RES two hours after intravenous liposome administration. Although longer circulation times are achieved with small unilamellar vesicles or SUVs (having a size range between about 0.03 and 0.08 microns), SUVs are generally less useful in drug delivery due to their smaller drug-carrying capacity, and their greater instability, which can lead to rapid release of liposome-associated drug, and to liposome fusion events that produce large and heterogeneous-size liposomes.

Several investigators, including the applicants, have also explored the possibility of increasing liposome circulation times by designing the liposome surface to mimic that of red blood cells. The role of cell surface carbohydrates in cellular recognition phenomena is widely appreciated (Ashwell, Hakormori, Karlsson). The chemistry, metabolism, and biological functions of sialic acid have been reviewed (Schauer). Surface sialic acid, which is carried by gangliosides, and glycoproteins such as glycophorin, plays an important role in the survival of erythrocytes, thrombocytes, and lymphocytes in circulation. Enzymatic removal of sialic acid, which exposes terminal galactose residues, results in rapid removal of erythrocytes from circulation, and uptake into Kupffer cells of the liver (Durocher). Desialylation of thrombocytes (Greenberg) and lymphocytes (Woodruff) also results in their rapid removal by the liver.

Although desialylated erthrocytes will bind to Kupffer cells or peritoneal macrophages in vitro in the absence of serum, serum must be added in order for significant phagocytosis to occur. The nature of the serum components mediating endocytosis is speculative, but immunoglobin and complement (C3b) are thought to be involved. Czop et al. (Czop) have shown that sheep erythrocytes, which are not normally phagocytosed by human monocytes, will bind C3b and be phagocytosed upon desialylation. Okada et al. (Okada) have demonstrated that sialyglycolipids on liposome membranes restrict activation of the alternative complement pathway and that removal of the terminal sialic acid from the glycolipids abolishes this restricting capacity and results in activation of the alternative complement pathway. Sialic acid, therefore, may be functioning as a non-recognition molecule on cell membranes partly through its ability to prevent binding of C3b, thus preventing phagocytosis via the alternative complement pathway. Other immune factors may also be involved in liposome phagocytosis. Alving has reported that 50% of the test sera from individual humans contain naturally occurring "anti-liposome" antibodies which mediated complement-dependent immune damage to liposomes.

The observations reported above suggest that surface sialic acid, and/or other red-cell surface agents, incorporated into liposomes, for example, in the form of ganglioside or glycophorin, may lead to increased circulation half-lives of liposomes. This approach is described, for example, in U.S. Pat. No. 4,501,728 for "Masking of Liposomes from RES Recognition", although this patent does not disclose whether significant RES making is actually achieved by coating liposomes with sialic acid.

In fact, experiments conducted in support of the present applications indicate that sialic acid, in the form of gangliosides, has a limited ability to extend circulation half lives in vivo in liposomes which are predominantly composed of conventional liposomes lipids, such as egg phosphatidylcholine (egg PC) or egg PC:cholesterol mixtures. In vivo uptake studies on PC:cholesterol:ganglioside liposomes (0.2 microns or smaller) indicate that the injected liposomes are localized predominantly in the RES two hours post administration.

In summary, several approaches for achieving enhanced liposome circulation times in the bloodstream have been proposed. Heretofore, however, the approaches have produced quite limited improvements in blood circulation times, particularly in liposomes in the 0.07–0.2 micron size range which are generally most desirable for parenteral drug compositions.

SUMMARY OF THE INVENTION

It is therefore one general object of the present invention to provide an improved liposome composition which gives significantly improved blood circulation times.

A more specific object of the invention is to provide such a composition in which liposomes are predominantly localized in the bloodstream, rather than in the liver and spleen, several hours after liposome administration.

Yet another object of the invention is to provide such a composition containing liposomes which are in a selected size range between about 0.08–0.2 microns.

Providing a method for significantly extending the lifetime of drug-carrying liposomes in the bloodstream, for improved drug delivery and/or drug targeting in tumor treatment is still another object of the invention.

The invention includes a liposome composition which is designed for enhanced circulation in the bloodstream. The liposomes in the composition are characterized by: (a) liposome sizes in a selected size range between about b 0.07 and 0.4 microns; (b) substantially homogenous-phase liposome bilayers composed of at least about 50 mole percent of a membrane-rigidifying lipid, and (c) between about 5–20 mole percent, hydrogenated phosphatidylinositol, (HPI). The acyl chains of the HPI serve to anchor the component in the liposome bilayers, without phase separation therein.

The liposomes show enhanced tissue distribution, as measured by the ratio of liposomal marker present in the blood to the combined amount of marker in the liver and spleen, when measured 2, 4, and 24 hours after intravenous liposome administration. Preferably, blood/RES ratio, when measured 2 hours after administration, is substantially greater than the sum of the blood/RES ratios obtained with similarly constructed liposome compositions containing in one case, at least about 50 mole percent of the membrane rigidifying lipid, but not the HPI, and in the other case, between 5-20 mole percent of the HPI, but not the membrane-rigidifying lipid.

In one preferred embodiment, the membrane-rigidifying lipid is a combination of sphingomyelin and a neutral phospholipid, such as phosphatidylcholine (PC), in a preferred molar ratio of between about 2:1 and 4:1. In another embodiment, the lipid is a saturated PC, with or without cholesterol.

The method of the invention is designed for extending the bloodstream lifetime of drug-containing liposomes which are administered intravenously in a suspension of liposomes whose sizes are in a selected size range between about 0.07-0.4 microns. The method includes preparing the liposomes to contain (a) at least about 50 mole percent of a membrane-rigidifying lipid in the liposome bilayers, which are substantially phase-homogeneous, and (b) between about 5-20 mole percent, hydrogenated phosphatidylinositol, (HIP).

The method gives significantly enhanced drug uptake in tumors, when administered intravenously to a tumor-bearing subject. The method is therefore useful in administering an anti-tumor compound for the treatment of the tumor by intravenous administration.

These and other objects and features of the invention will become more fully apparenet when the following detailed description of the invention is read in conjunction with the accompanying figures.

BRIEF DESCRIPTION OF THE DRAWINGS

FIG. 1 shows the time course of decrease of blood/RES ratios in a test subject injected IV with (1) liposomes containing ganglioside $GM_1$, but not SM (solid circles) and (2) with liposomes containing both $GM_1$ and SM (open circles);

FIGS. 2A and 2B show the effect of increasing molar amounts of $GM_1$ on percent injected liposome marker in blood (circles), liver (triangles), and spleen (squares) two hours post injection, in liposomes containing either PC:CH, 2:1 (A) or SM:PC, 4:1 (B)

DETAILED DESCRIPTION OF THE INVENTION

Figure 3A:
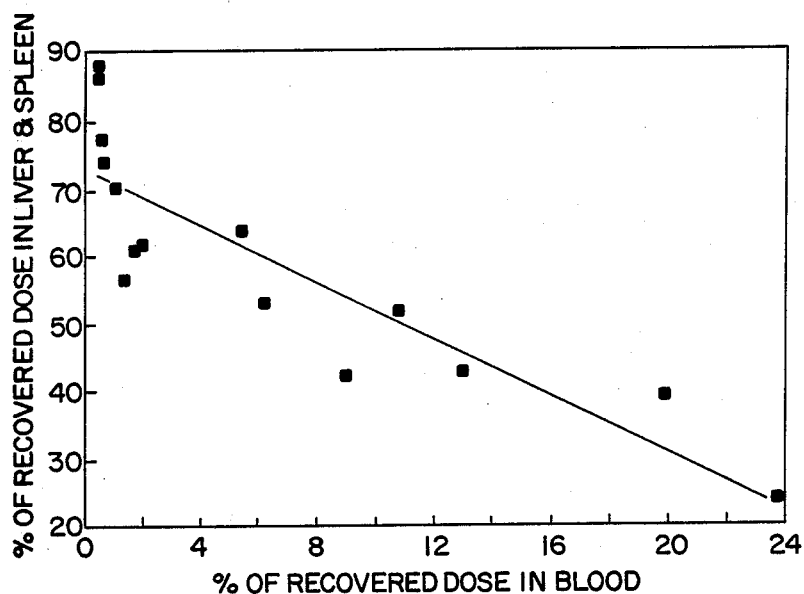
FIGS. 3A and 3B show linear regression plots of different liposome formulations for (A) liposomal marker in the RES versus the marker in the bloodstream, and (B) liposomal marker in the J6456 tumor (solid triangles) and B-16 tumor (solid circles) versus amount in the bloodstream.

The liposome composition of the invention is designed for delivering a drug or other agent, such as nutritional supplements, vitamins, or chelated metal, to a subject via the bloodstream, and for relatively slow uptake of the liposomes by the RES, allowing the drug or agent to be released from the liposomes into the bloodstream over an extended period of several hours or more. Alternatively, the composition is designed, by appropriate surface modification of the liposomes, for targeting via the bloodstream to non-RES target tissues, to allow the drug or agent to concentrate in the immediate region of the target tissue.

Section IA below describes the general method used to evaluate liposome uptake by the RES in vivo, section IB, the combination of liposome components which have been found, according to one aspect of the invention, to give high blood circulation times for intravenously injected lipsomes, and section IC, methods for preparing, sizing, and sterilizing drug containing liposomes designed for intravenous administration. The utility of the liposome composition, in drug delivery and drug targeting, is discussed in Section II.

I. PREPARING THE LIPOSOMAL COMPOSITION

A. Measuring liposome uptake by the RES in vivo

The method used for evaluating liposome circulation time in vivo measures the distribution of intravenously injected liposomes in the bloodstream and the primary organs of the RES at selected times after injection. In the standardized model which is used, RES uptake is measured by the ratio of total liposomes in the bloodstream to total liposomes in the liver and spleen, the principal organs of the RES. In practice, age and sex matched mice are injected intravenously (IV) through the tail vein with a radiolabeled liposome composition, and each time point is determined by measuring total blood and combined liver and spleen radiolabel counts, and in many studies, complete dissection, weighing, and radioactivity determinations of all body parts was done. Total blood counts are calculated by assuming that the total blood volume makes up 7% of the animal's body weight. Experimental methods are detailed in Example 2.

Since the liver and spleen account for nearly 100% of the initial uptake of liposomes by the RES, the blood/RES ratio just described provides a good approximation of the extent of uptake from the blood to the RES in vivo. For example, a ratio of about 1 or greater indicates a predominance of injected liposomes remaining in the bloodstream, and a ratio below about 1, a predominance of liposomes in the RES. For most of the lipid compositions of interest, blood/RES ratios were calculated at 2, 4, and 24 hours.

The data obtained with the model animal system can be reasonably extrapolated to humans and veterinary animals of interest. This is because, as mentioned above, uptake of liposomes by liver and spleen has been found to occur at similar rates in several mammalian species, including mouse, rat monkey, and human (Gregoriadis, 1974; Jonah; Kinelberg, 1976; Juliano; Richardson; Lopez-Berestein). This result likely reflects the fact that the biochemical factors which appear to be most important in liposome uptake by the RES-including opsinization by serum lipo proteins, size-dependent uptake effects, and cell shielding by surface moieties are common features of all mammalian species which have been examined.

B. Lipid Components

The lipid components used in forming the liposomes of the present invention are selected to meet three important criteria:

First, a major portion of the lipids, i.e., more than 50 mole percent, are neutral membrane-rigidifying components, by which is meant upcharged lipid components which produce relatively rigid, close-packed lipid bilayer structures. Typically, the lipids are predominantly saturated lipids whose phase transition temperature ($T_c$) is above about 25° C., and preferably between about 30° C. and 50° C. Preferred membrane-rigidifying lipids include SM ($T_c$ about 30° C.) and neutral phospholipids, such as PC whose acyl chains are predominantly saturated. One saturated PC which has been investigated extensively herein is distearoyl PC (DSPC) whose $T_c$ is about 50° C.

Figure 4:
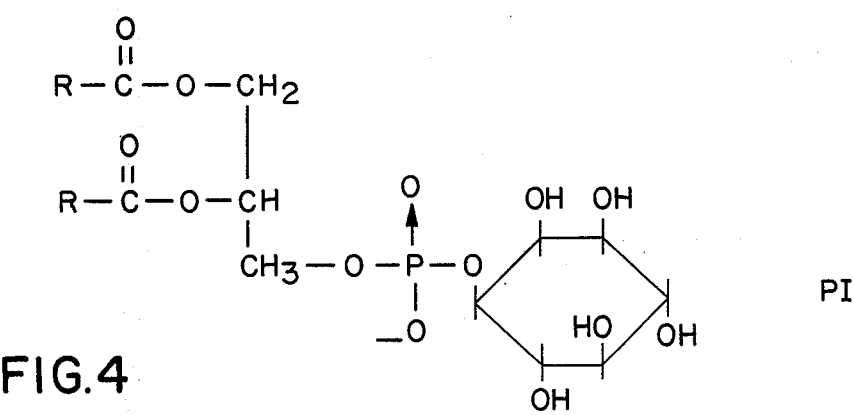
FIG. 4 shows the structural formula of HPI.

Secondly, and according to an important feature of the invention, the lipid components must contain hydrogenated phophatidylinositol (HPI), and whose structural formula is shown in FIG. 4.

Thirdly, the above lipid components must produce a substantially homogeneous-phase bilayer structure, by which is meant that the critical membrane rigidifying and HPI lipid components exist in a single phase, as opposed to discrete phases which are physically separate. As will be seen, this requirement both enhances blood/RES values achievable with the liposomes, and also minimizes rapid liposome breakdown and leakage in the bloodstream.

The importance of membrane-rigidying lipid components in combination with HPI can be appreciated from blood/RES data presented in Examples 8 and 9. The data here show that HPI, in the presence of saturated phospholipid (DSPC) and cholesterol, gives a blood/RES value which is about three times greater than that of liposomes composed of unsaturated PI and PC lipids and cholesterol.

Table 6 from Example 9 shows blood/RES values for a number of liposome compositions, as measured 24 hours post infection. The compositions are arranged according to increasing blood/RES values. It is apparent first that blood/RES values have declined significantly between 4 and 24 hours, but that the best formulations still show relatively good blood/RES values, e.g., 0.4 or higher, after 24 hours. These formulations include HPI, and $GM_1$ in combination with saturated PC (DSPC) plus cholesterol, in the presence or absence of SM.

The above-discussed data, and particularly the comparative data from Table 6, indicate that both $GM_1$ and HPI are effective, in combination with membrane-rigidifying components, in producing high blood/RES ratios.

In Table 5, it is seen that $GM_1$, SULF, and HPI all give comparable blood/RES values (about 1) in PC:CH liposome, whereas $GM_1$ and HPI (SULF was not tested) gave highest values with rigid-lipid components.

FIGS. 2A and 2B are plots of blood/RES values as a function of $GM_1$ mole ratio in two different liposome formulations. The first, shown in FIG. 2A, is a PC:CH formulation (which gives suboptimal blood/RES ratios), and the second, an SM:PC formulation. As discussed in Example 6, only the latter formulation shows a strong $GM_1$ effect. As seen, the optimal concentration of $GM_1$ is between 5-15 mole percent. The effect of high glycolipid concentration on blood/RES ratios is seen in Example 10, which examines 4 and 24 hour blood/RES ratios for liposomes containing DSPC:CH or PC;CH and increasing molar concentrations of HPI. Molar ratios of HPI above about 25% substantially eliminated the enhanced blood/RES values seen at concentrations of about 16 mole percent or below.

The requirement that the lipid components form a homogeneous-phase bilayer is aimed, in part, at ensuring good liposome stability in the bloodstream over a period of 24 hours or longer. Bilayer phase homogeneity should also contribute to improved blood/RES values, since liposome instability would be expected to enhance RES uptake. This may explain, for example, why the SM:$GM_1$ formulation has a relatively low blood/RES ratio after 24 hours (Table 6), yet gives a very high ratio after 2 hours (Table 1). The data from both tables indicate that this formulation is quite unstable and/or leaky in the bloodstream, as detailed in Example 9.

Phase inhomogeneity may also explain why PI is less effective than HPI in combination with DSPC:CH mixtures in enhancing blood/RES ratios, since HPI would be expected to be more phase-compatible (more similar $T_c$) with saturated PC.

In addition to the membrane-rigidifying agents and gangliosides required in the liposome composition, the liposomes may be formulated to include other neutral vesicle-forming lipids which do not significantly compromise the RES-evasion properties of the liposomes. An obvious example is cholesterol which is used in many of the above formulations above, at a mole ratio of about 30%.

The liposomes may also include protective agents such alpha-tocopherol, or other free-radical inhibitors, to minimize oxidative damage to the liposomes and/or entrapped drug carried in the liposomes.

C. Preparing the Liposome Composition

The liposomes may be prepared by a variety of techniques, such as those detailed in Szoka et al, 1980. One preferred method for preparing drug-containing liposomes is the reverse phase evaporation method described by Szoka et al and in U.S. Pat. No. 4,235,871. In this method, a solution of liposome-forming lipids is mixed with a smaller volume of an aqueous medium, and the mixture is dispersed to form a water-in-oil emulsion. The drug or other pharmaceutical agent to be delivered is added either to the lipid solution, in the case of a lipophilic drug, or to the aqueous medium, in the case of a water-soluble drug. Here it is noted that all lipid and aqueous components should preferably be sterile and pyrogen free. After removing the lipid solvent by evaporation, the resulting gel is converted to liposomes, with an encapsulation efficiency, for a water-soluble drug, of up to 50%. The reverse phase evaporation vesicles (REVs) have typical average sizes between about 2-4 microns and are predominantly oligolamellar, that is, contain one or a few lipid bilayer shells. The method is detailed in Example 1A.

The REVs are readily sized, as discussed below, by extrusion to give oligolamellar vesicles having a maximum selected size preferably between about 0.08 to 0.4 microns. Experiments conducted in support of the present invention indicate that sized oligolamellar vesicles of this type show substantially higher blood/RES ratios than similar sized multilamellar vesicles (MLVs), and that smaller REVs, e.g., 0.16-0.17 micron sizes, give higher ratios than larger REVs, e.g., 0.4 microns. Another advantage of REVs is the high ratio of encapsulated drug to lipid which is possible, allowing greater drug doses to be administered in a given lipid dose.

MLVs, where desired, can be formed by simple lipid-film hydration techniques. In this procedure, a mixture of liposome-forming lipids of the type detailed above dissolved in a suitable solvent is evaporated in a vessel to form a thin film, which is then covered by an aqueous medium. The lipid film hydrates to form MLVs, typically with sizes between about 0.1 to 10 microns. These vesicles, when unsized, show relatively poor blood/RES ratios, as seen in Table 9, for the unextruded MLV composition. Typically, MLVs are sized down to a desired size range of 0.5 or less, and preferably between about 0.07 and 0.12 microns by extrusion, as detailed below.

One effective sizing method for REVs and MLVs involves extruding an aqueous suspension of the liposomes through a polycarbonate membrane having a selected uniform pore size, typically 0.05, 0.08, 0.1, 0.2, or 0.4 microns (Szoka). The pore size of the membrane corresponds roughly to the largest sizes of liposomes produced by extrusion through that membrane, particularly where the preparation is extruded two or more times through the same membrane. This method of liposome sizing is used in preparing homogeneous-size REV and MLV compositions described in the examples below. A more recent method involves extrusion through an asymmetric ceramic filter. The method is detailed in U.S. patent application for Liposome Extrusion Method, Ser. No. 829,710, filed Feb. 13, 1986 and now U.S. Pat. No. 4,737,323.

Alternatively, the REV or MLV preparations can be treated to produce small unilamellar vesicles (SUVs) which are characterized by sizes in the 0.04–0.08 micron range. However, as indicated above, SUVs have a relatively small internal volume, for delivery of water-soluble drugs, and they tend to fuse to form larger heterogeneous size liposomes with heterodisperse drug leakage and RES uptake characteristics, and are leakier than REVs or MLVs. SUVs can be produced readily by homogenizing or sonicating REVs or MLVs, as described in Example 1C.

After final sizing, the liposomes can be treated, if necessary, to remove free (non-entrapped) drug. Conventional separation techniques, such as centrifugation, diafiltration, and molecular-sieve chromatography are suitable. The composition can be sterilized by filtration through a conventional 0.45 micron depth filter.

II. UTILITY

The significantly increased circulation half life of liposomes constructed as above can be exploited in two general types of therapeutic or diagnostic liposome compositions. The first composition is designed for sustained release of a liposome-associated agent into the bloodstream by circulating liposomes. As seen above, liposomes constructed according to the invention can be maintained predominantly in the bloodstream up to 24 hours, and therefore sustained release of the drug at physiologically effective levels for up to about 1 day or more can be achieved.

One measure of increased drug availability in the bloodstream is the increased area under the curve (AUC) seen with high blood/RES liposomes. The AUC measurement is made, as described in Example 9, by measuring liposome marker levels over a 24 hour period, for both blood and liver levels. The ratio of these AUC values then shows the extent to total liposome availability has been shifted from the liver to the bloodstream. Table 7 in Example 7 demonstrates that high blood/RES values are correlated with high AUC ratios.

The extended lifetime of the liposomes in the bloodstream also makes it possible for a significant fraction of the injected liposomes to reach the target site before being removed from the bloodstream by the RES. In particular, it is desired to target tumor tissue for drug treatment by intravenous administration to a tumor-bearing subject.

The use of the liposome composition of the invention for targeting animal tumors is detailed in Examples 11-13. Briefly summarizing the results, liposomes with increased blood/RES ratios produced a 10-30 fold enhancement in tumor uptake over free drug. Tumor uptake peaked at 24 hours post administration, although high levels of drug in the tumor were seen between 4 and 48 hours post administrations. Details of the treatment methods are given in the examples.

A variety of drugs or other pharmacologically active agents are suitable for delivery by the liposome composition. One general class of drugs include water-soluble, liposome-permeable compounds which are characterized by a tendency to partition preferentially into the aqueous compartments of the liposome suspension, and to equilibrate, over time, between the inner liposomal spaces and outer bulk phase of the suspension. Representative drugs in this class include terbutaline, albuterol, atropine methyl nitrate, cromolyn sodium, propranolal, flunoisolide, ibuprofen, gentamycin, tobramycin, pentamidine, penicillin, theophylline, bleomycin, etoposide, captoprel, n-acetyl cysteine, verapamil, vitamins, and radio-opaque and particle-emitter agents, such as chelated metals. Because of the tendency of these agents to equilibrate with the aqueous composition of the medium, it is preferred to store the liposome composition in lyophilized form, with rehydration shortly before administration. Alternatively, the composition may be prepared in concentrated form, and diluted shortly before administration. The latter approach is detailed in U.S. patent application for "Liposome Concentrate and Method", Ser. No. 860,528, filed May 7, 1986 and now abandoned.

A second general class of drugs are those which are water-soluble, but liposome-impermeable. For the most part, these are peptide or protein molecules, such as peptide hormones, enzymes, enzyme inhibitors, apolipoproteins, and higher molecular weight carbohydrates are characterized by long-term stability of encapsulation. Representative compounds in this class include calcitonin, atriopeptin, *a*-1 antitrypsin (protease inhibitor), interferon, oxytocin, vasopressin, insulin, interleukin-2, superoxide dismutase, tissue plasminogen activator (TPA), plasma factor 8, epidermal growth factor, tumor necrosis factor, lung surfactant protein, interferon, lipocortin, *a*-interferon and erythropetin.

A third class of drugs are lipophilic molecules which tend to partition into the lipid bilayer phase of the liposomes, and which are therefore associated with the liposomes predominantly in a membrane-entrapped form. The drugs in this class are defined by an oil/water partition coefficient, as measured in a standard oil/water mixture such as octanol/water, of greater than 1 and preferably greater than about 5. Representative drugs include prostaglandins, amphotericin B, progesterone, isosorbide dinitrate, testosterone, nitroglycerin, estradiol, doxorubicin, beclomethasone and esters, vitamin E, cortisone, dexamethasone and esters, and betamethasone valerate.

For sustained drug-release via the bloodstream, the liposome composition is administered intravenously in an amount which provides a suitable drug dosage over the expected delivery time, typically 12-24 hours. The injection may be given as a single bolus or slowly by i.v. drip, to allow gradual dispersal of the liposomes from the site of injection.

Where it is desired to target the liposomes to a selected non-RES tissue site, the liposomes are preferably designed for surface recognition of targetsite molecules. For example, in the case of targeting to a solid tumor, the liposomes may be prepared with surface-bound tumor recognition molecules, such as antibodies directed against tumor-specific antigens. Methods for coupling molecules of this type are wellknown to those in the field. These methods generally involve incorporation into the liposomes of lipid components, such as phosphatidylethanolamine, which can be activated for attachment of surface agents, or derivatized lipophilic compounds, such as lipid-derivatized bleomycin.

In one particular liposome composition which is useful for radioimaging of solid tumor regions, the liposomes are prepared with encapsulated radio-opaque or particle-emission metal, typically in a chelated form which substantially prevents permeation through the liposome bilayer, and carrying surface-bound bleomycin molecules, for preferential liposome attachment to tumor sites.

The following examples illustrate methods of preparing liposomes with enhanced circulation times, and for accessing circulation times in vivo and in vitro. The examples are intended to illustrate specific liposome compositions and methods of the invention, but are in no way intended to limit the scope thereof.

Ceramides (CER), cholesterol (CH), monogalactosyl-stearate sulfatides (SULF), galactocerebrosides (GAL), glucocerebrosides (GLU), and lactosylceremide (LAC) were obtained from Sigma (St. Louis, MO). Sphingomyelin (SM), egg phosphatidylcholine (lecithin) (PC), phosphatidylinositol (PI), hydrogenated phosphatidylinositol (HPI), phosphatidylserine (PS), phosphatidylglycerol (PG), phosphatidic acid (PA), phosphatidylethanolamine (PE), dipalmitoylphosphatidyl glycerol (DPPG), dipalmitoyl PC (DPPC), dioleyl PC (DOPC) and distearoyl PC (DSPC) were obtained from Avanti Polar Lipids (Birmingham, AL). Globosides (GLOB), digalactosyl diglyceride (DGDG), monosialoganglioside ($GM_1$), ganglioside $GM_2$ ($GM_2$), ganglioside $GM_3$ ($GM_3$), trisialoganglioside ($GT_{1b}$), and disialoganglioside ($GD_{1a}$) were obtained from Supelco (Bellefonte, PA).

[$^{125}$I]-tyraminyl-inulin was made according to published procedures. $^{67}$Gallium-8-hydroxyquinoline was supplied by NEN Neoscan (Boston, MA); doxorubicin (adriamycin), from Adria (Columbus, OH), and bleomycin, from Bristol Myers (Syracuse, NY).

EXAMPLE 1

Preparation of REVs, MLVs and SUVs

This example describes the preparation of reverse phase evaporation vesicles (REVs), multilamellar vesicles (MLVs) and small unilamellar vesicles (SUVs).

A. Sized REVs

A total of 50 mg of the selected lipid components, in the mole ratios indicated in the exanples below, were dissolved in 5 ml of diethyl ether. An aqueous buffer containing 13 mM phosphate, 140 mM NaCl, pH 7.4 was added to the organic solvent to a final volume of 6.5 ml, and the mixture was emulsified by sonication for 1 minute, maintaining the temperature of the solution at or below room temperature. Where the liposomes were prepared to contain encapsulated [$^{125}$I] tyraminyl-inulin, such was included in the phosphate buffer at a concentration of about 4 $\mu$Ci/ml buffer.

The ether solvent was removed under reduced pressure at room temperature, and the resulting gel was taken up in 1 ml of the above buffer, and shaken vigorously. The resulting REV suspension had particle sizes, as determined by microscopic examination, of between about 0.1 to 20 microns, and was composed predominantly of relatively large (greater than 1 micron) vesicles having one or only a few bilayer lamellae.

The liposomes were extruded twice through a polycarbonate filter (Szoka, 1978), having a selected pore size of 0.4 microns or 0.2 microns. Liposomes extruded through the 0.4 micron filter averaged 0.17 (0.05) micron diameters, and through the 0.2 micron filter, 0.16 (0.05) micron diameters. Non-encapsulated [$^{125}$I]-tyraminyl-inulin was removed by passing the extruded liposomes through Sephadex G-50 (Pharmacia).

B. MLVs

A total of 10-100 mg of the selected lipid components were dissolved in chloroform:methanol (2:1). The dissolved lipid was roto-evaporated to a thin film, then hydrated with an aqueous physiological buffer containing the solute, e.g., desferal or bleomycin, to be encapsulated. MLVs formed on gentle shaking for 1-2 hours. Non-encapsulated solute was removed by gel filtration. Examination of the MLVs showed heterogeneous sizes between about 0.1 to 20 microns, and a predominance of multilayered structures. The MLV's were sized by extrusion through a double polycarbonate membrane having a selected pore size. The membrane pore size was typically 0.05 micron for low phase transition (fluid) liposome formulations, and 0.08 micron for high phase transition (rigid) liposome formulations. In both cases, liposome sizes, as measured by laser light scattering, were predominantly in the 0.07-0.12 micron size range. When high phase transition lipids were used, rehydration and extrusion were carried at at 50°-60° C.

C. SUVs

About 25 ml of the unsized MLV suspension from above was sonicated by ultrasonic irradiation using a ½ inch sapphire-bonded probe, with pulse sonication during 15 minute intervals, under optimal output conditions. Sonication was carried out under a stream of nitrogen with the liposome vessel immersed in ice water. The sonicated vesicles were passed through Sephadex G-50 to remove released, free marker. Liposome sizes were predominantly in the 0.03-0.08 micron size range.

EXAMPLE 2

Measuring Blood/RES Levels

Age- and sex-matched mice, typically 20-15 g, were given intravenous injections of liposome suspensions or saline by injection into the tail vein. The total amount of material injected was about 0.5 mg phospholipid in a total injection volume of 0.2 ml. At selected time intervals following injection, the animals were sacrificed by cervical dislocation, blood samples were taken from the heart, and the liver and spleen were removed. The liver and spleen were blot dried, weighed and separately counted directly by gamma scintillation counting. A correction factor was applied to account for blood remaining in the liver and spleen. An aliquot of the blood sample was similarly counted by direct gamma counting. Total blood counts were calculated on the basis of a total blood volume of 7% body weight. The blood/RES ratio was calculated as total blood counts/total counts of the liver and spleen, and was frequently determined for several other tissues.

The blood/RES ratios measured over time were corrected for loss of liposomal radiolabel by multiplying the measured blood/RES ratio by the percent of the total counts remaining in vivo at each time point with respect to liposomal counts measured immediately after injection.

EXAMPLE 3

Relationship Between Lipid Composition and Blood/RES

REVs sized to 0.17 microns and having the liposome composition and mole ratios indicated at the left in Table 1 were prepared as in Example 1. The SM used for the reported studies was bovine brain sphingomyelin, whose hydrocarbon-chain moieties include a mixture of partially unsaturated chains. The liposomes were injected IV, and the injected animals were sacrificed two hours after injection. The table shows liposome sizes, blood/RES ratios, calculated as above, and percent of total of the total encapsulated marker (inulin) recovered at 2 hours post injection.

TABLE 1

| Composition | Size (μm) | Blood/RES | % remaining in vivo |
| --- | --- | --- | --- |
| 1 PC | 0.17 | 0.010 ± 0.005 | 86.0 ± 5.4 |
| 2 PC:CH, 2:1 | 0.17 | 0.13 ± 0.08 | 78.1 ± 0.04 |
| 3 PC:$GM_1$, 1:0.07 | 0.17 | 0.17 ± 0.12 | 79.4 ± 5.9 |
| 4 PC:CH:$GM_1$, 2:1:0.14 | 0.16 | 1.7 ± 0.5 | 75.6 ± 5.7 |
| 5 PC:CH:$ASGM_1$, 2:1:0.14 | 0.16 | 0.62 ± 0.44 | 64.8 ± 1.6 |
| 6 DSPC | 0.17 | 0.015 ± 0.002 | 91.2 ± 2.00 |
| 7 DSPC:CH, 2:1 | 0.17 | 0.007 ± 0.00 | 101.2 ± 2.4 |
| 8 DSPC:$GM_1$, 1:0.07 | 0.17 | 2.0 ± 0.02 | 76.7 ± 3.1 |
| 9 DSPC:CH:$GM_1$, 2:1:0.14 | 0.17 | 3.2 ± 1.0 | 64.6 ± 3.5 |
| 10 SM | 0.17 | 0.02 ± 0.01 | 27.1 ± 3.1 |
| 11 SM:CH, 2:1 | 0.17 | 0.7 ± 0.2 | 71.9 ± 4.4 |
| 12 SM:$GM_1$, 1:0.07 | 0.17 | 5.7 ± 1.8 | 12.4 ± 0.7 |
| 13 SM:CH:$GM_1$, 2:1:0.14 | 0.17 | 4.6 ± 0.6 | 72.1 ± 1.5 |
| 14 SM:PC, 4:1 | 0.17 | 0.6 ± 0.2 | 69.0 ± 3.3 |
| 15 SM:PC:CH, 4:1:3 | 0.17 | 0.12 ± 0.06 | 69.9 ± 2.2 |
| 16 SM:PC:CH:SULF, 4:1:3:0.35 | 0.17 | 0.43 ± 0.21 | 78.4 ± 1.4 |
| 17 SM:PC:$GM_1$, 4:1:0.35 | 0.16 | 3.3 ± 0.3 | 61.8 ± 2.9 |
| 18 SM:PC:CH:$GM_1$, 4:1:3:0.35 | 0.16 | 1.5 ± 0.6 | 88.5 ± 3.0 |
| 19 SM:PC:$ASGM_1$, 4:1:0.35 | 0.16 | 0.9 ± 0.5 | 80.3 ± 2.5 |

The blood/RES ratio data indicated that:

1. Ganglioside $GM_1$ in liposomes also containing a membrane-rigidifying component, such as cholesterol (composition 4), DSPC (composition 8), and SM (compositions 12, 17), or combinations of these lipid components (compositions 9 and 13) gave much higher blood/RES ratios than liposomes containing membrane rigidying components without $GM_1$ (compositions 6, 7, 10, 11, 14, or 15), or liposomes containing $GM_1$ but without membrane rigidifying components (composition 3).

2. Substituting asilaoganglioside ($ASGM_1$) for $GM_1$ in liposomes (composition 19 versus composition 17) largely abolished the $GM_1$ enhancement effect on blood/RES ratios.

The percent total recovery data show two SM formulations (compositions 10 and 12) which have relatively poor persistence in the body, presumably because of poor liposome stability and rapid clearance of the released encapsulated marker.

EXAMPLE 4

Effect of DSPC on Blood/RES

Sized REVs having the five lipid compositions shown at the left in Table 2, were prepared as above. The compositions are similar to several of the Table 1 compositions, except that distearoyl PC (DSPC) has been substituted for the relatively more unsaturated egg PC (PC). Blood/RES ratios were determined two hours after IV administration as in Example 3, with the results shown at the right in Table 2. A comparison of blood/RES vaues for comparable compositions in Tables 1 and 2 indicates that:

1. Substituting DSPC for PC in an SM:PC:$GM_1$ composition (composition 2 in Table 2 versus composition 17 in Table 1) significantly enhances the blood/RES ratio.

2. Substituting DSPC for PC in the SM:PC:CH:$GM_1$ composition (composition 5 in Table 2 versus composition 18 in Table 1) also enhances the blood/RES ratio.

TABLE 2

| Liposome composition | Blood/RES ratio |
| --- | --- |
| DSPC:$GM_1$, 5:0.35 | 1.8 |
| SM:DSPC:$GM_1$, 4:1:0.35 | 4.9 |
| SM:DSPC:$GM_1$, 1:1:0.14 | 3.7 |
| SM:DSPC:$GM_1$, 1:4:0.35 | 3.1 |
| SM:DSPC:CH:$GM_1$, 4:1:3:0.35 | 3.7 |

EXAMPLE 5

Time Course of Blood/RES over 24 Hours

Blood/RES ratios for two liposome compositions Sized (0.17 micron) REVs containing (1) PC:CH:$GM_1^*$, 2:1:0.14 (composition 4), and (2) SM:PC:$GM_1$, 4:1:0.35 (composition 17) were examined for blood/RES values at 2, 6 and 24 hours post injection. The behavior of the two formulations over a 24 hour period is shown in FIG. 1 for composition 4 (solid circles) and composition 17 (open circles).

As seen, composition 1 was substantially completely removed after 2 hours, whereas composition 2 retains a significant level in the blood even at 24 hours post injection.

EXAMPLE 6

Effect of Ganglioside Concentration on Blood/RES

Sized MLVs (0.17 microns) containing encapsulated inulin were prepared as above. The liposome compositions contained either PC:CH, 2:1 (FIG. 2A), or SM:PC, 4:1 (FIG. 2B) and increasing molar amounts of $GM_1$, including 0, 2.5, 5.0, 7.5, and 10, 12 and 15 mole percent. The tissue distribution of the liposome label in liver (triangles), spleen (squares), and blood (circles) were determined, as above, two hours post IV administration.

With reference to FIG. 2A, increasing molar amounts $GM_1$ increased blood levels two hours post injection to at most about 10%-of total injected counts in liposomes containing 5 and 7.5 mole percent ganglioside. At the same time, the lowest levels of liver uptake which were observed, also at 5 and 7.5 mole percent ganglioside, were greater than 30% of total injected counts.

By contrast, with reference to FIG. 2B, increasing amounts of $GM_1$ above about 2.5 mole percent increased the percent counts in the blood to above 50%, while total liver uptake fell to less than about 10%. The results demonstrate the importance of membrane-rigidifying components—in this case, SM—to the effect of $GM_1$ on blood/RES ratios. The results also show that optimal $GM_1$ concentrations of in the liposomes are between about 7.5 and 15.0 mole percent.

EXAMPLE 7

Effect of Sugar and Negatively Charged Groups on Blood/RES

Sized REVs having one of the 18 different compositions shown in Table 3 were prepared, to determine the effect of various sugar and/or negatively charged groups on blood/RES levels 2 hours after liposome administration. Each of the compositions contained PC:CH, 2:1 and 0.2 mole percent of one or more glycolipid or negatively charged lipid. The various charged and/or glycolipids used were: monogalactosyl-stearate, sulfatide (SULF) having a charged sulfate group on the galactose residue (FIG. 5c); phosphatidylserine (PS); phosphatidic acid (PA), ceramide trihexoside, (CTRI), an uncharged glycolipid with three hexose units; digalactosyl dglyceride (DGDG), an uncharged glycolipid with two galactosyl residues; monogalactosyl diglyceride (MGDG), an uncharged glycolipid with a single galactosyl residue; glactocerebrosides (GAL), an uncharged glycolipid with a single galactosyl residue; globosides (GLOB), an uncharged glycolipid with 4 sugar residues; asialoganglioside ($ASGM_1$); and glucocerebroside (GLU), an uncharged glycolipid with a single glucose residue.

The molar compositions, and blood/RES ratios measured for 2 hours post injection are given in Table 3 below. In the compositions containing PC and CH, only $GM_1$ or GAL or GLU in combination with $GM_1$ gave blood/RES values which are significantly greater than that given by PC:CH liposomes. PS and PA both decreased blood/RES ratios, with PS producing an extreme reduction in blood/RES.

In the composition containing SM and PC, monogalactosyl-stearate (SULF) gave values comparable to the PC:CH:$GM_1$ formulations.

TABLE 3

| Lipid composition* | size | blood/RES, 2 hrs post injection | % remaining in vivo |
|---|---|---|---|
| PC:CH, 2:1 | 0.1 μ | 0.68 ± 0.15 | 53.3 ± 6.6 |
| PC:CH:SULF, 2:12:0.2 | 0.1 μ | 0.54 ± 0.22 | 63.3 ± 1.3 |
| PC:CH:PS, 2:1:0.2 | 0.1 μ | 0.02 ± 0.00 | 79.2 ± 7.2 |
| PC:CH:PA, 2:1:0.2 | 0.1 μ | 0.09 ± 0.01 | 62.6 ± 2.2 |
| PC:CH:CTRI, 2:1:0.2 | 0.1 μ | 0.15 ± 0.02 | 81.7 ± 2.3 |
| PC:CH:DGDG, 2:1:0.2 | 0.1 μ | 0.74 ± 0.44 | 43.2 ± 7.2 |
| PC:CH:MGDG, 2:1:0.2 | 0.1 μ | 0.31 ± 0.08 | 67.4 ± 3.2 |
| PC:CH:GAL, 2:1:0.2 | 0.1 μ | 1.01 ± 0.63 | 8.7 ± 0.2 |
| PC:CH:GLOB, 2:1:02 | 0.1 μ | 0.08 ± 0.03 | 74.2 ± 2.1 |
| PC:CH:$ASG_{M1}$, 2:1:0.2 | 0.1 μ | 0.46 ± 0.01 | 75.2 ± 8.1 |
| PC:CH:GLU, 2:1:0.2 | 0.1 μ | 0.72 ± 0.21 | 84.6 ± 12.1 |
| PC:CH:$G_{M1}$, | 0.1 μ | 4.3 ± .1.1 | 75.9 ± 3.1 |
| PC:CH:GAL:$GM_1$, 2:1:0.2 | 0.1 μ | 5.95 ± 1.42 | 56.8 ± 5.0 |
| PC:CH:GLU:$GM_1$, 2:1:0.2 | 0.1 μ | 3.98 ± 0.91 | 81.3 ± 3.3 |
| SM:PC, 1:1 | 0.2 μ | 2.14 ± 1.36 | 72.05 ± 5.57 |
| SM:PC:SULF, 1:1:0.2 | 0.2 μ | 3.08 ± 3.41 | 82.4 ± 10.8 |
| SM:PC:PA, 1:1:0.2 | 0.2 μ | 1.20 ± 0.31 | 74.4 ± 2.9 |
| SM:PC:PS, 1:1:0.2 | 0.2 μ | 0.02 ± 0.00 | 81.3 ± 1.8 |

Blood/RES values were measured at 2 hours post injection for sized REVs (0.17 micron) composed of SM:PC, 4:1 and 0.35 mole percent of one of the following gangliosides or modified gangliosides: $GM_1$; $GM_2$, containing one less uncharged terminal sugar residue; $GM_3$, containing two less uncharged sugar residues; disialoganglioside ($GD_{1a}$), whose four sugar residues contain two sialic acid moieties; and trisialoganglioside ($GT_{1b}$), whose four sugar residues contain two sialic acid moieties. The blood/RES ratios are shown in Table 4 below. As seen, only the $GM_1$ ganglioside gives high blood/RES ratios.

TABLE 4

| Lipid composition | Blood/Res |
|---|---|
| SM:PC:$GM_1$ | 3.3 (0.3) |
| SM:PC:$GM_2$ | 0.6 (0.3) |
| SM:PC:$GM_3$ | 0.3 (0.2) |
| SM:PC:$GD_{1a}$ | 0.6 (0.3) |
| SM:PC:$GT_{1b}$ | 0.3 (0.3) |
| SM:PC:$ASGM_1$ | 0.9 (0.5) |

EXAMPLE 8

Liposome Distribution 4 Hours Post Injection

MLVs were prepared as in Example 1, using a hydration buffer containing 25 mM desferal. The lipid compositions are listed at the left in Table 5 below, and the relative molar quantities in the adjacent column. The MLVs were extruded as in Example 1, to produce a size range between about 0.07–1.12 microns, and free desferal was removed by Sephadex ™ G-75 column chromatography.

One day before animal injection, a complex of $^{67}$gallium/8-hydroxyquinoline (a weak lipophilic chelator) was added to the liposome suspension. When this complex penetrates the liposomes, $^{67}$Ga translocation to encapsulated desferal occurs. The resulting $^{67}$Ga-desferal complex has high affinity and is not diplaceable by transferrin or other metal-binding proteins. If released from liposomes, the complex is rapidly excreted through the urine with a half life of a few minutes. Immediately before injection, the liposomes are passed through an anion exchange resin (AG-1×4 acetate form) which completely removes all nonencapsulated $^{67}$Ga-8-hydroxyguinoline complex.

Age- and sex-matched mice were injected intravenously through the tail vein with a liposome preparation having one of the lipid compositions shown in Table 5 below. Four hours after injection, the levels of radioactivity (counts per minute) in blood and dissected body parts, including liver and spleen were measured by gamma counting, using integral counting between 10 and 1,000 kev. Total blood counts were determined as above, based on an estimated total blood volume. Percent total recovery was determined by whole body gamma counts (whole body counts×100/injected counts).

The blood/RES ratio was calculated as above, by dividing total blood counts by the sum of total liver and spleen counts, with the results shown in Table 5.

As seen, both $GM_1$ ganglioside and hydrogenated PI (HPI) gave relatively high blood/RES ratios in liposomes containing saturated PC or saturated PC plus SM. The same ganglioside or SULF in an unsaturated liposome formulation, or egg PI in an unsaturated formulation gave substantially lower values.

TABLE 5

| Liposome Composition | Molar Ratio of Components | Blood/RES Ratio | % Total Recovery |
|---|---|---|---|
| PG:PC:CH | 1:10:5 | .083 | 76.1 (0.8) |
| PG:PC:CH (unextruded) | 1:10:5 | .006 | 55.8 (2.9) |
| $GM_1$:PC:CH | 1:10:5 | 1.1 | 63.2 (2.0) |
| SULF:PC:CH | 1:10:5 | 1.1 | 61.0 (0.9) |
| DPPG:DSPC:CH | 1:10:5 | 2.0 | 88.6 (6.1) |
| PI:PC:CH | 1:10:5 | .83 | 49.0 (8.3) |
| HPI:DSPC:CH | 1:10:5 | 2.5 | 78.7 (1.5) |
| $GM_1$:SM:DSPC:CH | 1:8:2:5 | 5 | 50.3 (3.4) |
| $GM_1$:DSPC:CH | 1:10:5 | 5 | 88.5 (1.2) |
| $GL_4$:PC:CH | 1:10:5 | .02 | — |
| $GT_1$:PC:CH | 1:10:5 | .185 | — |

EXAMPLE 9

Liposome Distribution 24 hours Post Injection

Sized MLVs having the lipid compositions shown in Table 6 and encapsulating $^{67}$gallium/desferal complex were prepared as in Example 8. Blood/RES ratios and total percent body recovery, determined as above, are shown at the right in the table. The data show that $GM_1$, and HPI in combination with saturated neutral lipid components, such as DSPC and SM, give optimal blood/RES ratios at 24 hours.

Lower blood/RES values were obtained where the negatively charged component is PG or DSPG, in which the negative charge is shielded by the relatively small glycerol moiety; and cholesterol sulfate (CHS), in which the charged sulfate group is exposed.

TABLE 6

| Liposome Composition | Molar Ratio of Components | Blood/RES Ratio | % Total Recovery |
|---|---|---|---|
| $GT_1$:PC:CH | 1:10:5 | 0.004 | 58.2 (8.8) |
| PG:PC:CH (unextruded) | 1:10:5 | 0.004 | 31.3 (1.5) |
| $GL_4$:PC:CH | 1:10:5 | .008 | 34.3 (9.2) |
| PG:PC:CH | 1:10:5 | .008 | 49.8 (3.9) |
| DSPC:CH | 10:5 | .014 | 67.6 (4.2) |
| SULF:PC:CH | 1:10:5 | .02 | 41.6 (2.5) |
| SM:PC:CH | 8:2:5 | .03 | 21.9 (1.4) |
| SM:PC | 8:2 | .03 | 6.3 (1.2) |
| HPI:DOPC:CH | 1:10:5 | .06 | 46.3 (1.8) |
| CHS:DSPC:CH | 1:10:5 | .08 | 55.6 (6.0) |
| $GM_1$:SM:PC | 1:8:2 | .1 | 15.1 (0.5) |
| PC:CH | 10:5 | .11 | 44.4 (2.9) |
| $GM_1$:SM:PC:CH | 1:8:2:5 | .12 | 14.4 (1.9) |
| DPPG:DSPC:CH | 1:10:5 | .2 | 59.9 (5.5) |
| PG:DSPC:CH | 1:10:5 | .2 | 12.9 (1.4) |
| PI:PC:CH | 1:10:5 | .28 | 37.4 (6.3) |

TABLE 6-continued

| Liposome Composition | Molar Ratio of Components | Blood/RES Ratio | % Total Recovery |
|---|---|---|---|
| SULF:DSPC:CH | 1:10:5 | .3 | 57.5 (3.7) |
| $GM_1$:PC:CH | 1:10:5 | .33 | 40.3 (1.5) |
| HPI:DSPC:CH | 1:10:5 | .43 | 61.6 (4.0) |
| $GM_1$:SM:DSPC:CH | 1:8:2:5 | .5 | 36.9 (5.3) |
| HPI:HPC:CH | 1:10:5 | .55 | 51.1 (6.7) |
| $GM_1$:DSPC:CH | 1:10:5 | .9 | 66.3 (4.2) |

Also of note are the varied total body recoveries after 24 hours with the different formulations. Although there was no identifiable relationship between percent body recovery to blood or RES values, or their ratio, many of the formulations showed relatively low recoveries where the lipid components had widely varying phase transition temperatures ($T_p$). Thus, for example, the $GM_1$ formulations containing SM ($T_p$ about 30° C.) and DSPC ($T_p$ about 50° C.) gave much lower recovery than the formulation without SM, also as observed at 4 hours post injection. Even more striking was the low recovery seen for the ganglioside or non-ganglioside formulations containing SM and egg PC ($T_p$ about 0° C.), with or without cholesterol.

The total radioactivity levels (liposomal marker) contained in the blood, liver and spleen over a 24 hour post injection period were determined for several of the liposome compositions, shown at the right in Table 7 below. These levels were determined as area under the curve (AUC) for levels measured at 2, 4 and 24 hours, and thus are related to total levels of marker present in the tissue (blood, liver or spleen) in the period 24 hours post injection.

As seen from the table, high AUC blood/liver ratios were observed for the formulations containing $GM_1$ or HPI; and PG or DPPG formulations gave much lower ratios, consistent with the blood/RES ratios in Table 6.

TABLE 7

| Liposome Composition | Molar Ratio of Components | Blood Liver (AUC) | Blood/Liver AUC Ratio |
|---|---|---|---|
| PG:PC:CH | 1:10:5 | 0.52 7.34 | .07 |
| DPPG:DSPC:CH | 1:10:5 | 3.52 4.27 | .82 |
| $GM_1$:PC:CH | 1:10:5 | 2.66 1.68 | 1.58 |
| $GM_1$:SM:DSPC:CH | 1:8:2:5 | 2.21 1.76 | 1.25 |
| $GM_1$:DSPC:CH | 1:10:5 | 5.84 1.95 | 3.0 |
| HPI:DSPC:CH | 1:10:5 | 3.82 3.31 | 1.15 |

To examine whether a statistically significant correlation exists between liposome blood levels on one hand, and RES levels on the other, a linear regression analysis of the data, using the least squares method, was performed. FIG. 3A shows the inverse (negative) correlation between blood levels and RES uptake ($r=0.88$, $p=0.00002$). The values were taken from Table 6.

EXAMPLE 10

Effect of Charge on Blood/RES Ratios

Sized MLVs containing increasing molar amounts of HPI or PI and either DSPC or PC plus cholesterol, as indicated in Table 8 below, were prepared as above, and examined for blood/RES ratios and total body recovery 24 or 4 hours post injection. As seen, increasing the molar percentages of HPI from about 6 to 16 produced little change in the blood/RES ratio, whereas the ratio dropped dramatically between 16 and 30 percent. A similar drop in ratio was observed for the PI formulations, both 4 and 24 hours post injection. The percent PI or HPI had no major effect on total body recovery after 4 or 24 hours.

TABLE 8

| Liposome Composition | Molar Ratio of Components | % PI | Blood/RES Ratio | % Total Recovery |
|---|---|---|---|---|
| 24 Hours | | | | |
| HPI:DSPC:CH | 1:10:5 | 6.3 | .55 | 62.2 (6.0) |
| HPI:DSPC:CH | 2.5:7.5:5 | 16.7 | .45 | 59.9 (3.5) |
| HPI:DSPC:CH | 4.5:5.5:5 | 30.0 | .008 | 48.3 (1.5) |
| PI:PC:CH | 1:10:5 | 6.3 | .27 | 37.4 (6.3) |
| PI:PC:CH | 4:6:5 | 26.7 | .03 | 53.4 (15.3) |
| 4 Hours | | | | |
| PI:PC:CH | 1:10:5 | 6.3 | .83 | 49.0 (8.3) |
| PI:PC:CH | 4:6:5 | 26.7 | .07 | 72.4 (2.3) |

EXAMPLE 11

Uptake of Liposomal Marker into Mouse Tumors

Animals were inoculated with J6456 or B16 tumor cell lines. The J6456 line is a T-cell derived lymphoma (Gabizon) that will grow in vitro as a cell suspension, and after intraperitoneal injection, as an ascitic tumor. After IV injection, it will metastasize predominantly into the liver and spleen. The B16 melanoma line is a neuroectodermal-derived, solid type of tumor which grows as an adherent tumor in vitro, and metastasizes mainly in the lungs.

Tumor cells ($10^6$ J6456 or $5 \times 10^5$ B16 cells) were inoculated intramuscularly (IM) in the hind leg of syngeneic (C57BL/6 or Balb/c) female mice. Between 2-3 weeks after inoculation, when tumors weighed approximately 0.5 to 2 g, mice were injected IV with 1 umol phospholipid of one of the liposome compositions shown in Table 9 below. The molar ratios of components is the same as for the same-lipid component formulations. The liposomes were sized MLVs prepared as above with encapsulated gallium/desferal complex, and having sizes predominantly in the 0.07 to 0.12 micron size range.

Complete animal dissection followed 24 hours after liposome administration. The values shown in the table are based on $^{67}$gallium counts and corrected for blood content of the tissues. The correction factor for blood content in normal tissues and tumor was determined by examining the distribution of $^{111}$In-oxine-labeled red blood cells in age- and sex-matched tumor-bearing mice. Ratios were obtained by dividing the percents of injected dose per gram of respective tissues. Body average represents the average liposome uptake per gram body weight, and was calculated by dividing the percent of injected dose recovered in the total body (including tumor) by the weight of the animal.

As seen from the data in Table 9, for the J6456-injected mice, a steady increase in tumor uptake (up to 25 fold) was observed with liposomes selected for longer in vivo circulation times. Values of between about 4–6% of the injected dose were obtained with the formulations containing $GM_1$ ganglioside or with HPI in combination with saturated phospholipids. These values were obtained after correcting for blood volume in the tumor, as above. When free $^{67}$gallium-desferal complex was injected, the tumor uptake of the marker was less than 0.1% of the injected dose per gram. The data at the right in the table show a concomitant decrease in liver-to-tumor ratios, indicating that liposomes accumulate preferentially in tumors as opposed to non-specific enhancement in all body tissues. Progressively higher tumor-to-carcass ratio were also seen with the $GM_1$ or HPI formulations (data not shown).

TABLE 9

| Liposome Composition | Percent of Injected Dose/G (SD) | | | Ratio: Tumor/ Body Avg | Ratio: Liver/ Tumor |
|---|---|---|---|---|---|
| | Tumor | Liver | Body Avg | | |
| PG:PC:CH | 0.2 (0.0) | 36.4 (6.3) | 2.9 (0.7) | 0.1 | 182.0 |
| PG:PC:CH (unextruded) | 0.3 | 21.4 | 2.3 | 0.1 | 71.3 |
| SULF:PC:CH | 0.8 | 13.6 | 2.0 | 0.4 | 17.0 |
| DSPC:CH | 2.1 (0.3) | 36.5 (7.5) | 2.8 (0.3) | 0.8 | 17.4 |
| SULF:DSPC:CH | 2.1 (0.3) | 32.1 (4.5) | 2.1 (0.1) | 1.0 | 15.3 |
| CHS:DSPC:CH | 2.5 (0.1) | 29.7 (1.4) | 2.3 (0.2) | 1.1 | 11.9 |
| HPI:DSPC:CH | 4.1 (1.1) | 37.8 (0.4) | 3.0 (0.2) | 1.4 | 9.2 |
| DPPG:DSPC:CH | 4.1 (1.6) | 38.3 (0.5) | 2.8 (0.1) | 1.5 | 9.3 |
| $GM_1$:DSPC:CH | 5.3 (0.9) | 31.7 (1.4) | 3.3 (0.1) | 1.6 | 6.0 |
| $GM_1$:PC:CH | 3.5 (0.6) | 20.8 (0.9) | 2.4 (0.2) | 1.5 | 5.9 |

Similar conclusions are drawn from the tumor uptake data in animals inoculated with the B16, shown in Table 10, although tumor uptake increases as a function of liposome composition are less dramatic.

TABLE 10

| Liposome Composition | Percent of Injected Dose/G (SD) | | | Ratio: Tumor/ Body | Ratio: Liver/ Tumor |
|---|---|---|---|---|---|
| | Tumor | Liver | Body | | |
| $GM_1$:PC:CH | 2.5 (0.7) | 24.3 (1.3) | 2.5 (0.1) | 1.0 | 9.7 |
| SULF:DSPC:CH | 3.6 (0.8) | 23.5 (1.4) | 3.1 (0.3) | 1.2 | 6.5 |
| PG:DSPC:CH | 1.5 (0.4) | 9.8 (0.6) | 1.2 (0.2) | 1.3 | 6.5 |
| DSPC:CH | 5.4 | 33.2 | 4.2 | 1.3 | 6.1 |
| CHS:DSPC:CH | 5.7 (0.5) | 21.1 (1.9) | 3.5 (0.2) | 1.6 | 3.7 |
| DPPG:DSPC:CH | 4.9 (0.3) | 17.8 (2.2) | 2.9 (0.1) | 1.7 | 3.6 |
| $GM_1$:DSPC:CH | 8.4 (0.3) | 37.2 (7.2) | 4.4 (0.4) | 1.9 | 4.4 |
| HPI:DSPC:CH (1:10:5) | 5.3 (0.3) | 14.1 (0.3) | 2.9 (0.1) | 1.8 | 2.7 |
| HPI:DSPC:CH (2.5:7.5:5) | 5.2 (1.5) | 19.7 (2.1) | 3.3 (0.3) | 1.6 | 3.8 |
| HPI:DSPC:CH | .3 (1) | 44.1 (1.9) | 2.9 (0.1) | 0.1 | 147.0 |

TABLE 10-continued

| Liposome Composition | Percent of Injected Dose/G (SD) | | | Ratio: Tumor/ Body | Ratio: Liver/ Tumor |
|---|---|---|---|---|---|
| | Tumor | Liver | Body | | |
| (4.5:5.5:5) | | | | | |

Figure 3B:
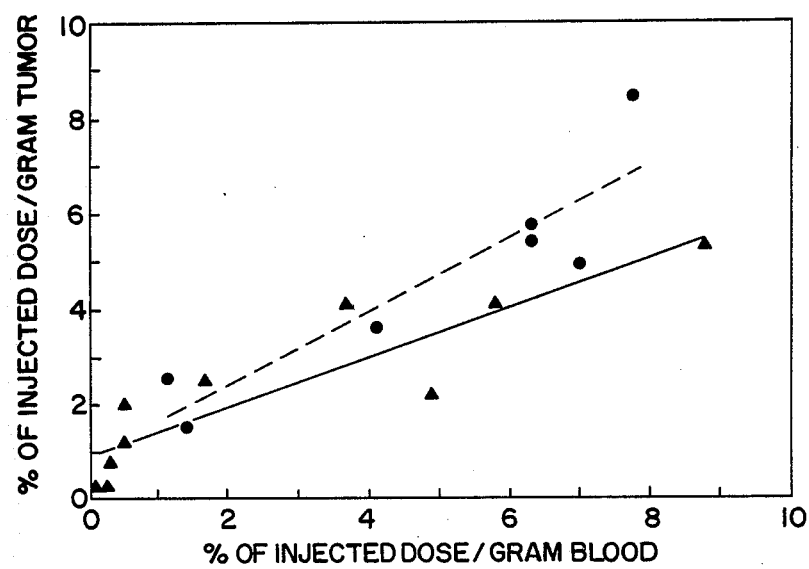

Linear regression analysis of the data, using least squares analysis, was carried out to determine whether a statistically significant correlation exists between liposome blood levels and tumor uptake. FIG. 3B shows a direct (positive) correlation between blood levels and tumor uptake of liposomes in both the B6456 (closed triangles) and B16 (closed circles) animals. The correlation coefficient for the J6456 animals are r=0.89 and p=0.0005, and for the B16 animals, r=0.91 and p=004.

EXAMPLE 12

Uptake of Indium-Labeled Bleomycin into Mouse Tumors

Sized MLVs composed of $GM_1$:DSP:CH (1:10:5) and containing encapsulated $^{111}$In-bleomycin were prepared as above. Bleomycin was labelled with $^{111}$In by adding the label to a suspension of bleomycin liposomes one day before liposome administration, to form a high-affinity, $^{111}$In-bleomycin complex encapsulated in the liposomes. Immediately before use the liposomes were passed through an anion-exchange resin, as above, to remove non-encapsulated $^{111}$In.

Mice innoculated with J6456 lymphoma or B16 cells were injected IV with liposomes (1 umole phospholpid/animal) or with an equivalent amount of free $^{111}$In-bleomycin. Tissue distribution of the radiolabel, 24 hours post administration, was determined as above, with the results shown in Tables 11 (J6456-infected animals) and Table 12 (B16-infected animals). As seen, the liposomal form of the drug increased drug quantity of 10-30 fold over free drug.

TABLE 11

| | Percent of Injected Dose /q Tissue | |
|---|---|---|
| TISSUE | FREE $^{111}$In-BLEO | $^{111}$In-BLEO |
| TUMOR | 0.7 | 8.2 (1.5) |
| BLOOD | 0.9 | 2.5 (0.9) |
| LIVER | 0.9 | 44.8 (0.6) |
| BODY AVG | 0.5 | 4.3 (0.1) |

TABLE 12

| | Percent of Injected Dose /q Tissue | |
|---|---|---|
| TISSUE | FREE $^{111}$In-BLEO | Liposomal $^{111}$In-BLEO |
| TUMOR | 0.3 (0.0) | 9.2 (1.9) |
| BLOOD | 0.1 (0.0) | 7.4 (0.8) |
| LIVER | 0.4 (0.0) | 23.0 (1.1) |
| BODY AVG | 0.2 (0.0) | 4.0 (0.3) |

Sized HPI:DSPC:CH (1:10:5) liposomes with encapsulated $^{111}$In-bleomycin were prepared as above and injected IV into mice inoculated with J6456 tumor cells, as above. Animals were sacrificed at 4, 24 and 48 hours and tumor, blood and liver levels of radioactivity determined, with the results shown in Table 13 below. Blood levels of the label dropped rapidly during the 4-48 hours test period. With both liver and tumor, optimal levels were observed at 24 hours, although both 4 and 48 hour levels were relatively high.

TABLE 13

| | Percent of Injected Dose /q Tissue | | |
|---|---|---|---|
| Tissue | 4 hours | 24 hours | 48 Hours |
| Blood | 47.9 (2.5) | 8 (1.5) | 0.7 (0.1) |
| Liver | 20.4 (1.6) | 30.6 (1.4) | 21.4 (0.8) |
| Tumor | 7.8 (1.2) | 13.7 (1.1) | 10.5 (0.7) |

EXAMPLE 13

Uptake of Doxorubicin into J6456 Mouse Tumors

Sized MLVs having one of the three lipid compositions shown in Table 14 below were prepared as above. Doxorubicin was included in the hydration buffer, at a concentration of about 5 mg/ml, and free drug was removed from the sized liposomes by gel filtration.

Mice innoculated with J6456 lymphoma cells were injected IV with the MLVs (1 umole phospholipid/animal) or with an equivalent amount of free doxorubicin. Tissue distribution of the drug, 24 hours post administration, was determined fluorometrically, with the results shown in Tables 13 below. As seen, drug levels of the drug, expressed as percent of injected dose/g tumor, were similar to free drug for the two liposome compositions (PG:PC:CH and $GM_{11}$:PG:PC:CH) which do not show significantly enhanced blood/RES ratios, whereas the drug level in tumors was enhanced 3-6 fold with $GM_1$:DSPC:CH liposomes which show optional blood/RES ratios.

TABLE 14

| Percent of Injected Dose (DXR)/q Tumor (SD) | |
|---|---|
| FREE DXR | 0.4 (0.1) |
| PG:PC:CH (DXR) (1:10:5) | 0.2 (0.0) |
| $GM_1$:PG:PC:CH (DXR) (1:10:5) | 0.2 (0.0) |
| $GM_1$:DSPC:CH (DXR) (1:10:5) | 1.3 (0.1) |

While specific methods of preparing and using the liposomes of the invention have been illustrated herein, it will be apparent that a variety of different lipid compositions, drug-liposome formulations, and liposome treatment methods can be practiced within the scope of the invention.

It is claimed:

1. A composition comprising liposomes which contain an entrapped pharmaceutical agent and are characterized by:
   (a) liposome sizes predominantly between about 0.05 and 0.5 microns,
   (b) liposomes having substantially homogeneous-phase bilayers composed at at least about 50 mole percent of a membrane-rigidifying lipid selected from the group consisting of sphingomyelin and neutral phospholipids with predominantly saturated acyl chains, and
   (c) between about 5-20 mole percent saturated phosphatidylinositol.

2. The composition of claim 1, wherein the liposomes are predominantly in the 0.07 to 0.12 micron size range.

3. The composition of claim 1, wherein the membrane-rigidifying lipid is brain sphingomyelin liposomes contain sphingomyelin and the liposomes contain sphingomyelin and phosphatidylcholine, at a mole ratio between 2:1 and 4:1.

4. The composition of claim 1, wherein the membrane-rigidifying lipid is predominantly phosphatidylcholine with saturated acyl chains.

5. In a therapeutic drug treatment in which a drug is administered intravenously in a suspension of liposomes in which the drug is entrapped and whose sizes are predominantly between about 0.05-0.5 microns, a method of extending the lifetime of liposomes in the bloodstream which comprises preparing the liposomes to contain:
(a) substantially homogeneous-phase bilayers containing at least about 50 mole percent of a membrane-rigidifying lipid selected from the group consisting of sphingomyelin and neutral phospholipids with predominantly saturated acyl chains, and
(b) between about 5-20 mole percent saturated phosphatidylinositol.

6. The method of claim 5, wherein the liposomes contain sphingomyelin and phosphatidylcholine, at a mole ratio between 2:1 and 4:1.

7. The method of claim 5, wherein the membrane-rigidifying lipid is predominantly phosphatidylcholine with saturated acyl chains.

8. The method of claim 5, for use in tumor therapeutic drug treatment, wherein the amount of drug which is delivered to the tumor, as measured by the amount drug/tumor weight 24 hours after drug administration, is severalfold greater than that achievable by administering the drug in free form.

9. The method of claim 8, wherein drug which is entrapped in the liposomes is bleomycin.

10. The method of claim 8, wherein the drug which is entrapped in the liposomes is doxorubicin.

11. The method of claim 8, which further includes targeting the liposomes to the tumor by addition of tumor-specific binding molecules to the liposome surfaces.

* * * * *

UNITED STATES PATENT AND TRADEMARK OFFICE
CERTIFICATE OF CORRECTION

PATENT NO. : 4,920,016
DATED : April 24, 1990
INVENTOR(S) : Theresa M. Allen; Alberto Gabizon It is certified that error appears in the above-identified patent and that said Letters Patent is hereby corrected as shown below:

Column 4, line 62 after the word "about" delete [b];

In the Detailed Description of the Invention:

Column 7, line 28, after "Examples 8 and 9." insert --Example 8 examines blood/RES ratios in several liposome compositions 4 hours post injection.--;

Column 7, line 49, after "ratios." insert --The ability of $GM_1$, in combination with membrane--rigidifying components, to produce high blood/RES ratios has been disclosed in parent co-pending application, now U.S. Patent No. 4,598,051. The present invention shows that a similar effect of HPI in liposomes formed predominantly of rigid-lipid membrane components.;

Column 12, line 56, change the numeral "15" to --25--;

Column 15, line 48, change "dglyceride" to --diglyceride";

Column 15, line 51, change "glactocerebrosides" to --galactocerebrosides--;

Column 15, line 66, change "composition" to --compositions--;

Column 21, line 17, change "p=004" to --p=0.004--;

Column 22, line 58, change "at" to --of--.

Signed and Sealed this

Thirteenth Day of August, 1991

*Attest:*

HARRY F. MANBECK, JR.

*Attesting Officer*     *Commissioner of Patents and Trademarks*